United States Patent [19]

Fanizzi et al.

[11] Patent Number: 4,849,545
[45] Date of Patent: Jul. 18, 1989

[54] PROCESS FOR THE PRODUCTION OF ALIPHATIC KETONES

[75] Inventors: Francesco P. Fanizzi, Bari, Italy; Peter M. Maitlis, Sheffield, United Kingdom

[73] Assignee: BP Chemicals Limited, London, England

[21] Appl. No.: 168,921

[22] Filed: Mar. 16, 1988

[30] Foreign Application Priority Data

Mar. 21, 1987 [GB] United Kingdom ............... 87067767

[51] Int. Cl.$^4$ ............................................. C07C 45/49
[52] U.S. Cl. .................................. 568/397; 568/407; 570/260
[58] Field of Search ................. 568/387, 407; 590/260

[56] References Cited

U.S. PATENT DOCUMENTS

| 3,137,715 | 6/1984 | Heck ..................................... 568/387 |
| 4,299,989 | 11/1981 | Dodds et al. ......................... 568/397 |

FOREIGN PATENT DOCUMENTS

| 600309 | 6/1960 | Canada ................................. 568/387 |
| 56-2925 | 1/1981 | Japan ..................................... 568/387 |
| 58-150533 | 9/1983 | Japan ..................................... 568/387 |

OTHER PUBLICATIONS

Patent Abstracts of Japan, (Field, Vol. 5, #494), 1981 56-2925.
Ito et al., Bull. Chem. Sat. Japan, vol. 50,(5), pp. 1319–1327, (1977).
Whitmire et al., Organometalics, vol. 5, pp. 987–994, (1986).
Saunders et al., J. Chem. Soc., Dalton Trans., p. 2473 (1983).
Miura et al., J. Chem. Soc., Chem. Comm, pp. 241–242, (1980).
Tanguy et al., Tet. Letters, vol. 25, pp. 5524–5532, (1984).

*Primary Examiner*—James H. Reamer
*Attorney, Agent, or Firm*—Brooks Haidt Haffner & Delahunty

[57] ABSTRACT

An aliphatic ketone is produced by reacting a carbonyl complex of a metal of Group VIII of the Periodic Table of the Elements, for example a rhodium carbonyl complex, with an aliphatic hydrocarbyl halide, for example an alkyl iodide.

6 Claims, No Drawings

PROCESS FOR THE PRODUCTION OF ALIPHATIC KETONES

The present invention relates in general to the production of ketones and in particular to a process for the production of aliphatic ketones, for example acetone.

Ketones are organic compounds containing one or more carbonyl groups and are represented by the general formula:

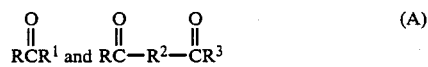
(A)

Depending on the nature of the hydrocarbon groups R—R³ attached to the carbonyl group(s) ketones are classified as symmetric or simple aliphatic, such as acetone $CH_3COCH_3$, symmetric aromatic such as benzophenone $C_6H_5COC_6H_5$, unsymmetric or mixed aliphatic-aromatic, such as methyl ethyl ketone $CH_3COC_2H_5$ and acetophenone $CH_3COC_6H_5$, alicyclic such as cyclopentanone, or heterocyclic. The present invention is concerned with the production of symmetric aliphatic, unsymmetric aliphatic and alicyclic ketones.

The lower aliphatic ketones are excellent solvents for nitrocellulose, vinyl resin lacquers, cellulose ethers and esters and various gums and resins. Because of their ability to form azeotropes with water and organic liquids, they are employed in extractive distillation.

Functionalised and cyclic ketones form metal complexes and are used as solvents and synthetic intermediates. Acetone, cyclohexanone, methyl ethyl ketone and methyl isobutyl ketone are among the hundred largest volume organic chemicals (in order of decreasing volume).

Ketones are produced on a commercial scale by a variety of methods. Acetone, the highest tonnage ketone, is produced either by the cumene hydroperoxide process, the direct oxidation of hydrocarbons, the catalytic oxidation of isopropyl alcohol or isopropyl alcohol dehydrogenation. In the cumene hydroperoxide process acetone is co-produced with phenol by alkylating benzene to cumene, which is oxidised to cumene hydroperoxide which, in turn, is cleaved to phenol and acetone. In a hydrocarbon oxidation process acetone is co-produced with, inter alia, $C_1$ to $C_4$ monocarboxylic acids by the air oxidation of, for example, naphtha. Acetone is also produced by the catalytic dehydrogenation of isopropanol (IPA). Although the selectivity of IPA vapour phase dehydrogenation to acetone is high there are a number of by-products that must be removed from the acetone. A clearly desirable objective would be to produce acetone as the principal product by a high selectivity, preferably catalytic, route from simple $C_1$ chemicals. It would also be desirable for the route to be applicable to the production of a range of ketones.

There have been many reports of the carbonylation of methyl-metal species to give acetone. Thus, for example, in Bull. Chem. Soc., Japan, 1977, 50, 1319, Ito et al disclose the reaction:

and in J. Chem. Soc., Dalton Trans., 1983, 2473, Saunders et al disclose the reaction:

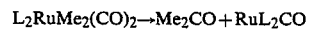

The above and most of the other reactions reported have required the prior synthesis of methyl-metal complexes, usually from a metal salt and a methyl Grignard or similar alkylating agent. It is doubtful whether such a reaction sequence could yield an economically viable catalytic route.

One possible exception to this general conclusion is the reaction reported by Whitmire et al in Organometallics, 1986, 5, 1987 entitled "Kinetics and Mechanism of the Reaction of [Et₄N][HFe(CO)₄] and Alkyl Halides. The Unexpected Formation of Acetone". In this reaction [HFe(CO)₄]⁻ is reacted with MeI at room temperature in acetonitrile solvent to produce methane as the principal product and some acetone in a very much slower subsequent reaction believed by the authors to be the reaction of MeI with product "Fe(CO)₄". The authors also report that in the presence of carbon monoxide the yield of acetone is reduced or eliminated.

Finally, U.S. Pat. No. 4,299,989 discloses a process for the production of a ketone which comprises treating a carboxylic acid ester in the presence of a catalyst comprising a compound containing a metal of Group VIII of the Periodic Table. In a specific embodiment of this process acetone is produced by treating methyl formate in the presence of a catalyst comprising chlororhodium phthalocyanine at a temperature in the range of from 50° to about 300° C. and a pressure in the range of from about 1 to about 300 atmospheres, said pressure being afforded by the presence of carbon monoxide, and in the added presence of dichlorobenzylalkyldimethylammonium chloride.

We have now to some extent fulfilled the aforesaid objective.

Accordingly, the present invention provides a process for the production of an aliphatic ketone which process comprises reacting a carbonyl complex of a metal of Group VIII of the Periodic Table of the Elements with an aliphatic hydrocarbyl halide.

As regards the metal of Group VIII of the Periodic Table the metal may suitably be a noble metal, i.e. rhodium, ruthenium, platinum, palladium, osmium or iridium, preferably rhodium, or other metal of Group VIII, for example cobalt. Any metal carbonyl complex may be employed. Suitably the metal carbonyl complex may be a neutral metal carbonyl complex as opposed to a metal carbonyl complex of the type [Et₄N][HFe(CO)₄]. An example of a suitable metal carbonyl complex is [Rh₂(CO)₄I₂]. Such complexes may be prepared by known methods.

The aliphatic hydrocarbyl halide may suitably be a hydrocarbyl monohalide of the formula RX(I) wherein in the formula (I) R is an aliphatic hydrocarbyl group and X is halide. The group R may suitably be linear-, branched or cycloaliphatic and may be substituted or unsubstituted. Using a hydrocarbyl monohalide the product ketone will generally be a symmetric aliphatic ketone or an alicyclic ketone. Using a mixture of hydrocarbyl monohalides it is possible to produced a mixture of ketones comprising symmetric and unsymmetric ketones. Preferably the group R in the formula (I) is an alkyl group, for example either methyl or ethyl. The halide moiety X of the hydrocarbyl halide may suitably be chloride, bromide or iodide, preferably iodide. Preferred hydrocarbyl halides include methyl iodide and ethyl iodide.

A preferred reaction is that of a rhodium carbonyl complex, for example [Rh$_2$(CO)$_4$I$_2$], with methyl iodide to produce acetone.

The process is preferably operated in the liquid phase, which may be provided either by the hydrocarbyl halide itself or by the addition of a suitable inert solvent. Suitable inert solvents include hydrocarbons and halohydrocarbons. Oxygenated solvents, for example ethers, may also be used if desired.

The process may be operated at ambient or elevated temperature, preferably at elevated temperature.

The process may be operated in an inert atmosphere or in the presence of carbon monoxide.

A catalyst may suitably be employed in the reaction.

In a preferred embodiment the present invention also provides a continuous process for the production of an aliphatic ketone which process comprises in a first step reacting a carbonyl complex of a metal of Group VIII of the Periodic Table with an aliphatic hydrocarbyl halide to produce an aliphatic ketone and a halide complex of the metal carbonyl and either (i) in a second step reacting the halide complex of the metal carbonyl with a compound of the formula ROR (II) wherein R is a hydrocarbyl group which is the same as the hydrocarbyl group of the hydrocarbyl halide and carbon monoxide to produce a product comprising the starting hydrocarbyl halide and the starting metal carbonyl and further reacting this product, or (ii) in a second step reacting the halide complex of the metal carbonyl with a hydrocarbylformate wherein the hydrocarbyl group is the same as the hydrocarbyl group of the starting hydrocarbyl halide to produce a product comprising the starting metal carbonyl complex and the starting hydrocarbyl halide and further reacting the product.

The aforesaid process applied to the production of acetone may be represented by the following reaction scheme:

M(CO)$_x$+MeI→MeCO-M(CO)$_{x-1}$I

MeCO-M(CO)$_{x-1}$I+MeI→Me$_2$CO+M(CO)$_{x-1}$I$_2$ either (i) M(CO)$_{x-1}$I$_2$+Me$_2$O+2CO→M(CO)$_x$+CO$_2$+2MeI or (ii) M(CO)$_{x-1}$I$_2$+2HCO$_2$Me→M(CO)$_2$+2MeI+H$_2$O+CO$_2$.

The invention will now be further illustrated by reference to the following Examples.

EXAMPLE 1

[RH$_2$(CO)$_4$I$_2$] and methyl iodide were charged to a tube and the tube sealed under an inert atmosphere. The tube was held at 60° C. for 24 hours. At the end of this period the tube was broken and the contents analysed. Acetone was obtained in a 90% stoichiometric yield.

EXAMPLE 2

The procedure of Example 1 was repeated except that ethyl iodide was used in place of methyl iodide and the temperature was held at 80° C. for 80 hours. Diethyl ketone was obtained in 50% yield.

EXAMPLE 3

A 100 ml Hastelloy autoclave was charged with rhodium dicarbonyl chloride dimer (0.1 g) and methyl iodide (25 ml) and pressurised to 40 bar with carbon monoxide. The autoclave was heated to 120° C. for 5 hours and then cooled in ice and discharged. GC analysis showed a small amount of acetone equivalent to the stoichiometric amount of acetone based on the rhodium charged.

We claim:

1. A process for the production of an aliphatic ketone which process comprises reacting a carbonyl complex of rhodium with an aliphatic hydrocarbyl halide having the formula RX wherein R is methyl or ethyl.

2. A continuous process for the production of an aliphatic ketone, which process comprises in a first step reacting a carbonyl complex of rhodium with a methyl or ethyl halide to produce an aliphatic ketone and a halide complex of the rhodium carbonyl, in a second step reacting the halide complex of the rhodium carbonyl with a dimethyl or diethyl ether and carbon monoxide to produce a product comprising the starting methyl or ethyl halide, and thereafter reacting the product of the second step.

3. A continuous process for the production of an aliphatic ketone which process comprises in a first step reacting a carbonyl complex of rhodium with a methyl or ethyl halide to produce an aliphatic ketone and a halide complex of the rhodium carbonyl, in a second step reacting the halide complex of the rhodium carbonyl with a methyl or ethyl formate to produce a product comprising the starting rhodium carbonyl complex and the starting methyl or ethyl halide, and thereafter reacting the product of the second step.

4. A process according to claim 1 wherein the carbonyl complex of rhodium is a neutral complex.

5. A process according to claim 5 wherein the neutral complex is [Rh$_2$(CO)$_4$I$_2$].

6. A process according to claim 1 wherein a rhodium carbonyl complex is reacted with methyl iodide to produce acetone.

UNITED STATES PATENT AND TRADEMARK OFFICE
CERTIFICATE OF CORRECTION

PATENT NO.  : 4,849,545

DATED       : July 18, 1989

INVENTOR(S) : Francesco P. Fanizzi and Peter M. Maitlis

It is certified that error appears in the above-identified patent and that said Letters Patent is hereby corrected as shown below:

Col. 3, l. 41, formula should read "$M(CO)_{x-1}I+$"

Col. 3, lines 44-45, formula should read "$(CO)_{x+}2MeI$"

Signed and Sealed this

Fourth Day of December, 1990

Attest:

HARRY F. MANBECK, JR.

*Attesting Officer*   *Commissioner of Patents and Trademarks*